United States Patent [19]

Gerdes et al.

[11] Patent Number: 5,100,859

[45] Date of Patent: Mar. 31, 1992

[54] CATALYST CARRIER

[75] Inventors: William H. Gerdes, Hudson; Carmine M. Doddato, Cuyahoga Falls, both of Ohio; Patrick F. Malone, Phoenix, Ariz.

[73] Assignee: Norton Company, Worcester, Mass.

[21] Appl. No.: 643,604

[22] Filed: Jan. 22, 1991

[51] Int. Cl.$^5$ ............................................. B01J 32/00
[52] U.S. Cl. .................................. 502/439; 502/242; 502/250
[58] Field of Search ............... 502/236, 242, 202, 250, 502/439

[56] References Cited

U.S. PATENT DOCUMENTS

| | | | |
|---|---|---|---|
| 2,357,254 | 8/1944 | Danforth | 502/202 |
| 2,834,738 | 5/1958 | Vincent | 502/202 |
| 3,006,909 | 10/1961 | Witt | 502/242 |

Primary Examiner—Carl F. Dees
Attorney, Agent, or Firm—David Bennett

[57] ABSTRACT

The invention relates to catalyst carries for use in conjunction with silver, alkali metal promoters, rhenium promoters and optionally rhenium co-promoters selected from sulfur, nolybdenum, tungsten, chromium and mixtures thereof. The carriers consisting of at least 85 and preferably 95 percent by weight of alpha alumina, from about 0.01 to about 6 percent by weight of an alkaline earth metal silicate and from about zero to about 10 percent by weight (measured as the dioxide of added zirconium in the form of an oxide.

10 Claims, No Drawings

CATALYST CARRIER

FIELD OF THE INVENTION

The invention relates to a novel alpha alumina carrier useful in conjunction with silver-containing catalysts in the preparation of ethylene oxide.

BACKGROUND OF THE INVENTION

Catalysts for the production of ethylene oxide from ethylene and molecular oxygen generally comprise silver supported on a carrier formed substantially of alpha alumina. Such catalysts are typically promoted with alkali metals. Other co-promoters, such as rhenium, or rhenium along with sulfur, molybdenum, tungsten and chromium can also be utilized. See, for example, U.S. Pat. No. 4,766,105, issued Aug. 23, 1988. While much research has been focused on promoters, more recently, work has been focused on the alumina supports and ways to modify them to produce improved catalysts.

European Patent Application 247,414, published Dec. 2, 1987, discloses the addition of silica to an alpha alumina carrier. U.S. Pat. No. 4,428,863, issued Jan. 31, 1984, discloses the addition of barium aluminate or barium silicate to alumina carriers during their manufacture. In U.S. Pat. No. 4,728,634, issued Mar. 1, 1988, silicon dioxide and an alkali metal salt are mixed with water and an aluminum compound and calcined to produce a silica- and alkali metal-containing alpha alumina support. In U.S. Pat. No. 4,874,739, Oct. 17, 1989, a tin compound and an alkali metal compound are incorporated into an alpha alumina carrier.

SUMMARY OF THE INVENTION

The invention relates to an alpha alumina based carrier comprising at least about 85% by weight of alpha alumina, from about 0.01 to about 6% by wt. (measured as the oxide) of an alkaline earth metal oxide which is defined to include mixed oxides such as the preferred silicate; from 0.01 to about 5% by weight, (measured as silica) of a silicon oxide, including mixed oxides such as the silicates, and from zero to about 10% by wt. (measured as the oxide) of a zirconia oxide.

Preferred carrier compositions comprise the alkaline earth metal and the silicon containing compounds in the form of a single compound, an alkaline earth metal silicate, which may be added as an original component or generated in situ by the reaction of silica or silica generating compounds with compounds that decompose to the alkaline earth metal oxide upon heating, with the amount of the oxide formed being in stoichiometric excess over the silica so as to leave essentially no residual base-soluble silica in the final composition other than that contributed by impurities present in the alumina.

While the alkaline earth metal component of the catalyst can be chosen from magnesium, calcium, strontium and barium, the preferred embodiments are calcium and magnesium with the former the most preferred. In the further description of this invention reference will frequently be made to the calcium form for the sake of simplicity.

The preferred carriers may be prepared by mixing a powdered alpha alumina, calcium silicate and zirconia with water and a binder and/or burnout material to prepare a mixture which is then extruded and calcined at a temperature ranging from about 1350° C. to about 1500° C.

DESCRIPTION OF THE PREFERRED EMBODIMENTS

The novel carrier of the invention may be prepared from high purity alpha alumina powder, an alkaline earth metal oxide-providing compound, a silica-providing compound, an optional zirconia-providing compound and conventional binders/burnout agents.

The alpha alumina used in the carrier preparation generally has a purity greater than about 98%, preferably greater than about 98.5% and less than about 0.06% by weight such as from 0.02 to 0.06% by weight of soda impurities. The alumina has the form of a fine powder, preferably one having an average particle size of from about 0.5 to about 5 microns and more preferably from about 1 to about 4 microns. The average crystallite size, which can be from about 0.1 to about 5 microns and more preferably from about 2 to about 4 microns, is determined by measuring the maximum dimension of a number of crystallites and taking the average thereof. The alpha alumina will be present in the calcined carrier in an amount greater than about 85%, preferably 90, and more preferably 95% by weight of the total carrier.

The alkaline earth metal component of the carrier composition of the invention this can be present in an amount that represents from 0.01 to about 6% by weight (measured as the oxide, MO,) of the carrier weight but preferably the amount present is from about 0.03 to about 5.0% and especially from about 0.05 to about 4.0% by weight. Where calcium or magnesium is alkaline earth metal, the amount present is preferably 0.05 to 2% by weight. Where a silicate is formed in situ, the weights of the components used should be selected with these limitations in mind and so as to avoid the presence of base-soluble silica in the finished composition.

The alkaline earth compounds that may be used to prepare the carriers of the invention are oxides or compounds that are decomposable to or which form oxides upon calcination. Examples include carbonates, nitrates, and carboxylates. Other suitable compounds include the oxides themselves, and mixed oxides such as the aluminates, silicates, aluminosilicates, zirconates and the like. The preferred compounds are calcium oxide and calcium silicate.

The silicon compounds used to prepare the carriers of the invention are oxides or compounds decomposable to the oxides upon calcination. Suitable compounds include silicon dioxide itself, as well as the mixed oxides such as the alkaline earth metal silicates, zirconium silicates, aluminosilicates such as zeolites, hydrolyzable silicon compounds, polysiloxanes and the like. The amount used should be such as to provide, in the final carrier composition, from about 0.01 to about 5.0%, such as from about 0.03 to about 4.0% and most conveniently from about 0.05 to about 3.0% by weight, (measured as silica).

The zirconia component, while optional, is preferably present in an amount that is from about 0.01 to about 10.0%, such as from about 0.3 to about 5.0% and especially from about 0.05 to about 2.0% by weight based on the carrier weight. Where the zirconia is generated in situ, the amount used should be selected to give a final proportion within these parameters.

The zirconium compounds which may be used to prepare the carriers are oxides or compounds which are decomposable to or which form oxides upon calcination. Examples include carbonates, nitrates and carboxylates. Suitable compounds include zirconium nitrate, zirconium dioxide, as well as the mixed oxides such as zirconium silicates, zirconium aluminosilicates, zirconates and the like. The preferred compound is zirconium dioxide.

The alpha alumina powder is most preferably combined with calcium silicate itself but, as indicated above, it is also possible to use a calcium oxide-generating compound and silica or a silica-generating compound in such proportions that on heating calcium silicate is produced with essentially no base soluble silica. These components are mixed with zirconia or a zirconia-generating compound, (where present), a burnout/binding agent and water, formed into shapes and calcined.

The burnout agent is a material that is added to the mixture such that upon calcination, it is completely removed from the carrier, leaving a controlled porosity in the carrier. These materials are carbonaceous materials such as coke, carbon powders, graphite, powdered plastics such as polyethylene, polystyrene and polycarbonate, rosin, cellulose and cellulose based materials, sawdust and other plant materials such as ground nut shells, e.g. pecan, cashew, walnut and filbert shells. Carbon-based binding agents can also serve as burnout agents. The burnout agents are provided in an amount and size distribution to provide a final carrier having a water pore volume preferably ranging from about 0.2 to 0.6 cc/g. Preferred burnout agents are cellulose-derived materials, such as ground nut shells.

The term "binding agent" as used herein refers to an agent that holds together the various components of the carrier prior to calcination to form an extrudable paste, i.e, the so-called low temperature binding agent. The binding agent also facilitates the extrusion process by adding lubricity. Typical binding agents include alumina gels, particularly in combination with a peptizing agent such as nitric or acetic acid. Also suitable are the carbon based materials that can also serve as burnout agents, including celluloses and substituted celluloses such as methylcellulose, ethylcellulose and carboxyethylcellulose, stearates such as organic stearate esters, e.g. methyl or ethyl stearate, waxes, polyolefin oxides and the like. Preferred binding agents are polyolefin oxides.

The use of calcium silicate, whether prepared directly or in situ with the constraints described above, allows the use of bonds containing, overall, a lower amount of silica then is present in conventional bonds. It also permits the avoidance of an excess of silicon dioxide which typically contains deleterious amounts of sodium, iron and/or potassium impurities, especially when present in clays, bentonite and the like.

The role of the zirconia, where used, is not fully understood but it appears to stabilize certain partial oxidation catalyst recipes. Calcium silicate also appears to stabilize at least a proportion of the zirconia in the more active tetragonal form instead of the monoclinic form to which the mixed phase reverts when heated in the absence of calcium silicate.

After the components of the carrier are mixed together, say by mulling the mixed material is extruded into shaped pellets, for example, cylinders, rings, trilobes, tetralobes and the like. The extruded material is dried to remove water that would convert to steam during calcination and destroy the physical integrity of the extrudate shapes. Typically the drying and calcination are combined in one step by suitable programming of the time and temperature. Calcining is carried out under conditions sufficient to remove burnout agents and binding agents and to fuse the alpha alumina particles into a porous, hard mass. Calcination is typically carried out in an oxidizing atmosphere, say oxygen gas or preferably air and at a maximum temperature over 1300° C. and preferably ranging from about 1350° C. to about 1500° C. Times at these maximum temperatures can range from about 0.5 to about 5 hours.

The calcined carriers will typically have pore volumes (water) ranging from about 0.2 to about 0.6, and more preferably from about 0.3 to about 0.5 cc/g, and surface areas ranging from about 0.15 to about 3.0, and preferably from about 0.3 to about 2.0 m$^2$/g.

The carrier formulation preferably has a low soda content which is less than about 0.06% by wt. In practice it is very difficult to obtain a sodium-free formulation and soda contents from about 0.02 to 0.06% by wt. are usually found acceptable.

The carriers described above are particularly suited for preparing ethylene oxide catalysts which have high initial selectivities and long lives (enhanced stability).

In a preferred application of silver catalysts carried on carriers according to the present invention, ethylene oxide is produced when an oxygen-containing gas is contacted with ethylene in the presence of the catalyst-/carrier at a temperature in the range of from about 180° C. to about 330° C. and preferably about 200° C. to about 325° C.

The ranges and limitations provided in the instant specification and claims are those which are believed to particularly point out and distinctly claim the instant invention. It is, however, understood that other ranges and limitations that perform substantially the same function in substantially the same way to obtain the same or substantially the same result are intended to be within the scope of the instant invention as defined by the instant specification and claims.

ILLUSTRATIVE EMBODIMENTS

Carrier Preparation

Carrier A:

An alpha alumina powder having the properties listed in Table 2 below was used to prepare the carrier.

TABLE 2

| | |
|---|---|
| Median Particle Size | 3.0–3.4 microns |
| Average Crystallite Size | 1.8–2.2 microns |
| Soda Content | 0.02–0.06% by wt. |

This powder was used to prepare a formulation of the following ceramic components:

| | |
|---|---|
| Alpha Alumina | 98.8% |
| Zirconia | 1.0% |
| Calcium Silicate | 0.2% |

Based on the weight of this formulation, the following were added in the indicated proportions:

| | |
|---|---|
| Burn-out (walnut shell flour) | 25.0% |
| Boric Acid | 0.1% |
| Extrusion Aid* | 5.0% |

*Polyolefin oxide

After the above had been mixed for 45 seconds, enough water was added to give an extrudable mixture, (about 30% in practice), and mixing was continued for a further 4 minutes. At this point 5% (based on the weight of the ceramic components), of vaseline was added and mixing was continued for a further 3 minutes.

This material was extruded in the form of 5/16×5/16 inch hollow cylinders and dried to less than 2% moisture. These were then fired in a tunnel kiln to a maximum temperature of 1390° C. for about 4 hours.

After processing in this manner the carrier had the following properties:

| | |
|---|---|
| Water Absorption | 40.8% |
| Crush Strength | 18.7 lbs. |
| Surface Area | 0.56 m²/gm. |
| Total Pore Volume (Hg) | 0.43 cc/gm. |
| Median Pore Diameter | 4.6 microns |

Leachable Cations (in nitric acid) in ppm:

| | |
|---|---|
| Na | 141 |
| K | 55 |
| Ca | 802 |
| Al | 573 |
| $SiO_2$ | 1600 |

Additional carriers were prepared in a manner similar to the method described above with the exception that different starting materials were used. The properties of the different starting aluminas are shown in Table 3 below.

TABLE 3

Properties for Aluminas Nos. 11 and 49

| | #11 | #49 |
|---|---|---|
| Median Particle Size | 3.0–3.6 | 3.0–4.0 microns |
| Average Crystallite size | 1.6–1.8 | 1.0–1.4 microns |
| Soda Content | 0.02–0.06% | 0.02–0.06% by wt. |

The water pore volumes, surface areas and firing temperatures are shown in Table 4 and the other starting materials and their amounts are shown in Table 5 below.

A comparative carrier was made with alumina #10 in the same manner described above for carrier A except that no zirconia or calcium silicate were added. This comparative carrier was denoted as Com-A. Its properties are provided in Table 4 below.

TABLE 4

| Carrier | Pore Vol. cc/gm | Surface Area m²/gm (water) | Firing Temp. Degrees C. |
|---|---|---|---|
| Com-A | 0.46 | 0.52 | 1371 |
| A | 0.41 | 0.54 | 1388 |
| B | 0.42 | 0.52 | 1371 |
| C | 0.39 | 0.49 | 1371 |
| D | 0.34 | 0.60 | 1371 |
| E | 0.26 | 0.16 | 1371 |
| F | 0.30 | 0.34 | 1371 |
| G | 0.27 | 0.25 | 1371 |
| H | 0.35 | 0.57 | 1454 |
| I | 0.43 | 0.60 | 1400 |
| J | 0.44 | 0.51 | 1393 |
| K | 0.37 | 0.50 | 1371 |
| L | 0.42 | 0.59 | 1371 |
| M | 0.38 | 0.51 | 1371 |
| N | 0.44 | 0.73 | 1371 |
| O | 0.42 | 0.74 | 1371 |
| P | 0.50 | 0.66 | 1413 |
| Q | 0.47 | 0.68 | 1413 |
| R | 0.51 | 0.81 | 1413 |
| S | 0.43 | 0.45 | 1413 |
| T | 0.43 | 0.38 | 1413 |
| U | 0.54 | 1.09 | 1413 |
| V | 0.55 | 0.66 | 1413 |
| W | 0.54 | 0.98 | 1413 |
| X | 0.42 | 0.41 | 1400 |
| Y | 0.47 | 0.60 | 1400 |
| Z | 0.41 | 0.44 | 1371 |
| AA | 0.40 | 0.46 | 1371 |

TABLE 5

| Carr. | Alumina | Compound A* | Compound B* | Compound C* |
|---|---|---|---|---|
| Com-A | #10 | | | |
| A | #10 | $ZrO_2$ (1.0) | $CaSiO_3$ (0.20) | |
| B | #10 | $ZrO_2$ (1.0) | $CaSiO_3$ (0.10) | |
| C | #10 | $ZrO_2$ (1.0) | $CaSiO_3$ (0.40) | |
| D | #10 | | $CaSiO_3$ (0.40) | |
| E | #10 | | $CaSiO_3$ (0.20) | |
| F | #10 | $ZrO_2$ (1.0) | $CaSiO_3$ (2.00) | |
| G | #10 | $ZrO_2$ (1.0) | $CaSiO_3$ (4.00) | |
| H | #10 | $ZrO_2$ (1.0) | $CaAlSiO_6$ (0.20) | |
| I | #10 | $ZrO_2$ (1.0) | $Ca(NO_3)_2$ (0.28) | $SiO_2$ (0.10) |
| J | #10 | $ZrO_2$ (1.0) | $Ba(NO_3)_2$ (0.47) | $ZrSiO_4$ (0.31) |
| K | #10 | $ZrO_2$ (1.0) | $CaSiO_3$ (0.20) | $Ca(NO_3)_2$ (0.29) |
| L | #10 | $ZrO_2$ (1.0) | $MgSiO_3$ (0.20) | |
| M | #10 | $ZrO_2$ (1.0) | $MgSiO_3$ (2.20) | |
| N | #10 | $ZrO_2$ (1.0) | $Mg_3Al_2(SiO_4)_3$ (0.20) | |
| O | #10 | $ZrO_2$ (1.0) | $SrSiO_3$ (2.20) | |
| P | #49 | $ZrO_2$ (1.0) | $CaSiO_3$ (0.30) | |
| Q | #49 | $ZrO_2$ (1.0) | $CaSiO_3$ (0.30) | $Ca(NO_3)_2$ (0.29) |
| R | #49 | $ZrSiO_4$ (0.46) | $Ca(NO_3)_2$ (0.44) | |
| S | #49 | $ZrSiO_4$ (0.46) | $Ca(NO_3)_2$ (0.73) | |
| T | #49 | $ZrSiO_4$ (0.46) | $Ca(NO_3)_2$ (1.02) | |
| U | #49 | $ZrSiO_4$ (0.46) | $Ca(NO_3)_2$ (0.70) | |
| V | #49 | $ZrSiO_4$ (0.46) | $Ca(NO_3)_2$ (1.17) | |
| W | #49 | $ZrSiO_4$ (0.46) | $Ca(NO_3)_2$ (1.63) | |
| X | #11 | $ZrO_2$ (1.0) | Mullite (0.07) | $Ca(No_3)_2$ (0.22) |
| Y | #11 | $ZrO_2$ (1.0) | Mullite (0.07) | $Ca(No_3)_2$ (0.13) |
| Z | #10 | $ZrO_2$ (5.0) | $CaSiO_3$ (0.20) | |
| AA | #10 | $ZrO_2$ (10.0) | $CaSiO_3$ (0.20) | |

*Weight percent basis alumina

Catalyst Preparation

Carrier A described above is a preferred carrier and was used to prepare an ethylene oxide catalyst. Into a solution of water and ethylenediamine were dissolved silver oxalate, cesium hydroxide, ammonium perrhenate, lithium sulfate and lithium nitrate in amounts sufficient to provide in the impregnated carrier (basis dry weight of carrier) 13.2% wt silver, 440 ppm cesium, 1.5 micromoles/g of ammonium perrhenate, 1.5 micromoles/g of lithium sulfate and 4 micromoles/g of lithium nitrate. Approximately 30 g of the carrier were placed under 25 mm vacuum for 3 minutes at room temperature. Approximately 50 g of the impregnating solution were then introduced to submerge the carrier, and the vacuum was maintained at 25 mm for an additional 3 minutes. At the end of this time, the vacuum was released, and the excess impregnating solution was removed from the carrier by centrifugation for 2 minutes at 500 rpm. The impregnated carrier was then cured by being continuously shaken in a 300 cu.ft./hr. air stream at 250° C. for 5 minutes. The cured catalyst, denoted as C-A', is ready for testing.

The actual silver content of the catalyst can be determined by any of a number of standard, published procedures. The actual level of rhenium on the catalysts prepared by the above process can be determined by extraction with 20 Mm aqueous sodium hydroxide solution, followed by spectrophotometric determination of the rhenium in the extract. The actual level of cesium on the catalyst can be determined by employing a stock cesium hydroxide solution, which has been labeled with a radioactive isotope to cesium, in catalyst preparation. The cesium content of the catalyst can then be determined by measuring the radioactivity of the catalyst. Alternatively, the cesium content of the catalyst can be determined by leaching the catalyst with boiling deionized water. In this extraction process cesium, as well as the other alkali metals, is measured by extraction from the catalyst by boiling 10 grams of whole catalyst in 20 milliliters of water for 5 minutes, repeating the above two more times, combining the above extractions and determining the amount of alkali metal present by comparison to standard solutions of reference alkali metals using atomic absorption spectroscopy (using Varian Techtron Model 1200 or equivalent). It should be noted that the cesium content of the catalyst as determined by the water leaching technique may be lower than the cesium content of the catalyst as determined by the radiotracer technique.

The carriers listed in Table 4 and 5 were used to prepare the catalysts listed in Table 6. C-A and C-A' refer to a catalyst prepared with carrier A, C-B and C-B' refer to a catalyst prepared with carrier B, etc.

TABLE 6

| Catalyst | Ag Wt % | Cs ppm | NH$_4$ReO$_4$ umol/g | Li$_2$SO$_4$ umol/g | LiNO$_3$ umol/gC- |
|---|---|---|---|---|---|
| C-Com-A | 13.2 | 501 | 1.5 | 1.5 | 4 |
| C-A | 13.5 | 463 | 1.5 | 1.5 | 4 |
| C-A' | 13.5 | 437 | 1.5 | 1.5 | 12 |
| C-B | 13.2 | 506 | 1.5 | 1.5 | 4 |
| C | 13.2 | 480 | 1.5 | 1.5 | 4 |
| C-D | 13.2 | 470 | 1.5 | 1.5 | 4 |
| C-E | 10.0 | 274 | 0.75 | 0.75 | 4 |
| C-F | 12.0 | 277 | 1.0 | 1.0 | 4 |
| C-G | 12.0 | 306 | 1.0 | 1.0 | 4 |
| C-H | 13.4 | 589 | 1.5 | 1.5 | 4 |
| C-I | 13.2 | 665 | 2.0 | 2.0 | 4 |
| C-J | 14.5 | 468 | 1.5 | 1.5 | 4 |
| C-K | 13.2 | 442 | 1.5 | 1.5 | 4 |
| C-L | 13.2 | 540 | 1.5 | 1.5 | 4 |
| C-L' | 13.2 | 481 | 1.5 | 0 | 4 |
| C-M | 13.2 | 415 | 1.5 | 1.5 | 4 |
| C-M' | 13.2 | 382 | 1.5 | 0 | 4 |
| C-N | 14.5 | 620 | 1.5 | 1.5 | 4 |
| C-N' | 14.5 | 573 | 1.5 | 0 | 4 |
| C-O | 14.5 | 547 | 1.5 | 1.5 | 4 |
| C-P | 14.5 | 599 | 2.0 | 2.0 | 4 |
| C-Q | 14.5 | 572 | 1.5 | 1.5 | 4 |
| C-R | 14.5 | 795 | 2.0 | 2.0 | 4 |
| C-S | 13.2 | 510 | 1.5 | 1.5 | 4 |
| C-T | 13.2 | 520 | 1.5 | 1.5 | 4 |
| C-U | 14.5 | 887 | 2.0 | 2.0 | 4 |
| C-V | 14.5 | 750 | 2.0 | 2.0 | 4 |
| C-W | 14.5 | 786 | 2.0 | 2.0 | 4 |
| C-X | 13.3 | 500 | 1.5 | 1.5 | 4 |
| C-Y | 14.5 | 620 | 1.5 | 1.5 | 4 |

The Process

The following describes the standard microreactor catalyst test conditions and procedures used to test the catalyst for the production of ethylene oxide from ethylene and oxygen.

Three to five grams of crushed catalyst (14–20 mesh) are loaded into a 0.23 inch diameter stainless steel U-shaped tube. The U tube is immersed in a molten metal bath (heat medium) and the ends are connected to a gas flow system. The weight of catalyst used and the inlet gas flow rate are adjusted to achieve a gas hourly space velocity of 3300 cc of gas per cc of catalyst per hour. The inlet gas pressure is 210 psig.

The gas mixture passed through the catalyst bed (in once-through operation) during the entire test run (including startup) consists of 30% ethylene, 8.5% oxygen, 5–7% carbon dioxide, 54.5% nitrogen, and 0.5 to 5 ppmv ethyl chloride.

The initial reactor (heat medium) temperature is 180° C. After one hour at this initial temperature, the temperature is increased to 190° C. for one hour, followed by 200° C. (1 hour), 220° C. (1 hour), 227° (2 hours), 235° C. (2 hours), and 242° C. (2 hours). The temperature is then adjusted so as to achieve a constant oxygen conversion level of 40% ($T_{40}$). The moderator level is varied and run for 4–24 hours at each level to determine the optimum moderator level for maximum selectivity. Performance data at the optimum moderator level and at $T_{40}$ are usually obtained when the catalyst has been onstream for a total of about 24 hours and are provided in the examples given below. Due to slight differences in feed gas composition, gas flow rates, and the calibration of analytical instruments used to determine the feed and product gas compositions, the measured selectivity and activity of a given catalyst may vary slightly from one test run to the next.

To allow meaningful comparison of the performance of catalysts tested at different times, all catalysts described in this illustrative embodiment were tested simultaneously with a standard reference catalyst. All performance data reported in this illustrative embodiment are corrected to conform to the average initial performance of the reference catalyst which was $S_{40}=81.0\%$ and $T_{40}=230°$ C.).

The catalysts prepared above were tested using the above procedure and the results are given in the table below.

TABLE 7

| Catalyst | $S_{40}$'% | $T_{40}$, °C. |
|---|---|---|
| C-Com-A | 85.1 | 261 |
| C-A | 85.8 | 258 |
| C-A' | 86.0 | 258 |
| C-B | 86.3 | 261 |
| C-C | 85.8 | 256 |
| C-D | 86.5 | 259 |
| C-E | 83.8 | 266 |
| C-F | 85.6 | 259 |
| C-G | 85.0 | 276 |
| C-H | 85.9 | 267 |
| C-I | 85.2 | 263 |
| C-J | 84.2 | 262 |
| C-K | 87.4 | 258 |
| C-L | 87.1 | 250 |
| C-L' | 87.3 | 252 |
| C-M | 86.8 | 260 |
| C-M' | 86.0 | 252 |
| C-N | 87.0 | 257 |
| C-N' | 85.2 | 257 |
| C-O | 87.1 | 265 |
| C-P | 84.3 | 247 |
| C-Q | 85.5 | 252 |
| C-R | 86.6 | 260 |
| C-S | 83.8 | 250 |
| C-T | 85.7 | 264 |
| C-U | 82.9 | 254 |
| C-V | 83.5 | 260 |
| C-W | 81.9 | 252 |
| C-X | 85.9 | 254 |
| C-Y | 85.3 | 258 |

We claim:

1. A carrier composition suitable for preparing silver-based ethylene oxide catalysts comprising at least 85% by weight of alpha alumina, from 0.01 to about 6.0% by weight (measured as the oxide, MO where M is an alkaline earth metal,) of an alkaline earth metal oxide, from 0.01 to about 5.0% by weight (measured as silica) of a silicon oxide, and from zero to about 10% by weight (measured as the dioxide) of zirconium in the form of an oxide.

2. A carrier composition according to claim 1 comprising at least 85 percent by weight of alpha alumina, from about 0.01 to about 6.0% by weight of an alkaline earth metal silicate and from about 0.01 to about 10 percent by weight of zirconia.

3. A carrier composition according to claim 2 comprising at least 95 percent by weight of alpha alumina, from about 0.03 to about 4 percent by weight of calcium silicate and from about 0.3 to about 5 percent by weight of zirconia, the composition being essentially free of base-soluble silica.

4. A carrier composition according to claim 1 having a surface area ranging from about 0.15 to about 3.0 square meters per gram and a water pore volume ranging from about 0.2 to about 0.6 cubic centimeters per gram.

5. A carrier composition according to claim 1 which is essentially free of base-soluble silica.

6. A carrier composition according to claim 1 in which the alumina has a soda content of less than 0.06% by weight.

7. A process for preparing a carrier suitable for use in preparing silver-based, rhenium promoted ethylene oxide catalysts which comprises:
    (a) mixing:
        (i) an alpha alumina powder having a purity of greater than about 98 percent and having an average crystallite size between 0.1 and about 5 microns;
        (ii) an alkaline earth metal oxide or compound which is decomposable to or forms oxide upon calcination;
        (iii) a silicon oxide or compound which is decomposable to or forms an oxide upon calcination; and optionally
        (iv) a zirconium oxide or compound which is decomposable to or forms an oxide upon calcination, with water and a binder/burnout agent in amounts sufficient to provide in the finished carrier alpha alumina in an amount greater than about 85 percent by weight, an alkaline earth metal oxide in an amount ranging from about 0.01 to about 6.0% by weight, silicon oxide in an amount ranging from about 0.01 to about 5.0% by weight, and, optionally, zirconium oxide in an amount ranging from zero to about 10.0% by weight;
    (b) extruding the resulting mixture of step (a) to form pellets; and
    (c) calcining the pellets at a temperature greater than 1300° C. for a time sufficient to produce a carrier having a surface ranging from about 0.3 to about 2 square meters per gram and a water pore volume ranging from about 0.2 to about 0.6 cubic centimeters per gram.

8. A process according to claim 7 in which the amounts of the components are selected to give a carrier composition comprising at least 90% by weight of alumina, from about 0.03 to about 5.0% by weight of an alkaline earth metal oxide, from about 0.03 to about 4.0% by weight of a silicon oxide and from about 0.3 to about 5.0% by weight of zirconia, the relative proportions being selected so that there is essentially no base-soluble silica in the final carrier composition.

9. A process according to claim 8 in which the alkaline earth metal compound and the silicon oxide are selected such that, after calcination, they are present in the form of a single compound.

10. A process for preparing a carrier suitable for use in preparing silver-based, rhenium promoted ethylene oxide catalysts which comprises:
    (a) mixing with water and a binder/burnout agent in amounts sufficient to provide in the finished carrier alpha alumina in an amount greater than about 95 percent by weight, calcium silicate in an amount ranging from about 0.05 to about 4 percent by weight, and zirconium oxide in an amount ranging from about 0.3 to about 5 percent by weight;
    (b) extruding the resulting mixture of step (a) to form pellets; and
    (c) calcining the pellets at a temperature greater than 1300° C. for a time sufficient to produce a carrier having a surface ranging from about 0.3 to about 2 square meters per gram and a water pore volume ranging from about 0.2 to about 0.6 cubic centimeters per gram.

* * * * *